US009988639B2

(12) United States Patent
Takayama et al.

(10) Patent No.: US 9,988,639 B2
(45) Date of Patent: Jun. 5, 2018

(54) **METHOD FOR BREEDING *BRASSICA RAPA* PLANT HAVING SELF-COMPATIBILITY**

(71) Applicant: NATIONAL UNIVERSITY CORPORATION NARA INSTITUTE OF SCIENCE AND TECHNOLOGY, Nara (JP)

(72) Inventors: Seiji Takayama, Nara (JP); Eiko Uno, Nara (JP)

(73) Assignee: NATIONAL UNIVERSITY CORPORATION NARA INSTITUTE OF SCIENCE AND TECHNOLOGY, Ikoma-Shi, Nara (JP)

( * ) Notice: Subject to any disclaimer, the term of this patent is extended or adjusted under 35 U.S.C. 154(b) by 21 days.

(21) Appl. No.: 14/763,143

(22) PCT Filed: Jan. 20, 2014

(86) PCT No.: PCT/JP2014/050958
§ 371 (c)(1),
(2) Date: Jul. 23, 2015

(87) PCT Pub. No.: WO2014/115680
PCT Pub. Date: Jul. 31, 2014

(65) Prior Publication Data
US 2015/0353946 A1    Dec. 10, 2015

(30) Foreign Application Priority Data
Jan. 24, 2013 (JP) ................. 2013-011504

(51) Int. Cl.
*A01H 1/02* (2006.01)
*C12N 15/82* (2006.01)
*C12Q 1/68* (2018.01)
*A01H 5/10* (2018.01)

(52) U.S. Cl.
CPC ........... *C12N 15/8231* (2013.01); *A01H 1/02* (2013.01); *A01H 5/10* (2013.01); *C12Q 1/6895* (2013.01); *C12N 15/8218* (2013.01); *C12N 15/8287* (2013.01); *C12Q 2600/13* (2013.01); *C12Q 2600/158* (2013.01)

(58) Field of Classification Search
None
See application file for complete search history.

(56) References Cited

U.S. PATENT DOCUMENTS 8,026,417 B2 *  9/2011  Thoonen .................. A01H 5/10
                                                         800/264

OTHER PUBLICATIONS

Fujimoto et al. Plant Molecular Biology 61: 577-597 (2006).*
Shen et al. Plant Breeding 124: 111-116 (2005).*
Bi et al. Molecular and General Genetics 263: 648-654 (2000).*
Sato et al. Plant Cell Physiology 47(3): 340-345 (2006).*
Isokawa et al. Genes and Genetic Systems 85: 87-96 (2010).*
Kitashiba et al. Breeding Science 64: 23-37 (2014).*
Okamoto S. et al., Self-compatibility in *Brassica napus* is caused by independent mutations in S-locus genes, The Plant Journal, 2007, vol. 50, p. 391-400.
Tarutani Y. et al., Trans-acting small RNA determines dominance relationships in Brassica self-incompatibility., Nature, 2010, vol. 466, Iss.7309, p. 983-986.
Shiba H. et al., Epigenetic regulation of monoallelic gene expression., Develop. Growth Differ., 2012, vol. 54, No. 1, p. 120-128.
Tarutani Y. et al., "Aburana no Jikafuwagosei ni Okeru small RNA o Kaishita Yuretsusei Kiko", Cell Technology, 2010, vol. 29, No. 12, p. 1254-1256.
Tarutani Y. et al., "New Molecular Mechanism Underlying Dominance Relation-ships", Seibutsu to Kagaku, 2011, vol. 49, No. 10, p. 678-682.
Fujimoto R. et al., Molecular Mechanisms of Epigenetic Variation in Plants., Int. J. Mol. Sci., 2012, vol. 13, No. 8, p. 9900-9922.
Osabe K. et al., Multiple Mechanisms and Challenges for the Application of Allopolyploidy in Plants., Int. J. Mol. Sci., 2012, vol. 13, No. 7, p. 8696-8721.
Zhang X. et al., Progress on characterization of self-incompatibility in *Brassica napus* L., Euphytica, 2011, vol. 182, p. 147-155.
Finnegan E.J. et al., Self-incompatibility: Smi silences through a novel sRNA pathway., Trends in Plant Science, 2011, vol. 16, No. 5, p. 238-241.

* cited by examiner

*Primary Examiner* — David T Fox
(74) *Attorney, Agent, or Firm* — Knobbe, Martens, Olson & Bear, LLP

(57) ABSTRACT

The problem of providing a technology that converts a *Brassica rapa* plant having self-incompatibility to having self-compatibility is addressed. The problem is solved by causing a pollen factor (SP11) to be inactive at a self-incompatibility gene locus for a *Brassica rapa* plant, while maintaining the inverted repeat sequence (SMI) on a class I dominant S haplotype.

4 Claims, 4 Drawing Sheets

SEQUENCE LISTING

```
<160> NUMBER OF SEQ ID NOS: 23

<210> SEQ ID NO 1
<211> LENGTH: 24
<212> TYPE: DNA
<213> ORGANISM: Brassica rapa

<400> SEQUENCE: 1
atgtttacgt gtaaaatagt taca                                              24

<210> SEQ ID NO 2
<211> LENGTH: 74
<212> TYPE: PRT
<213> ORGANISM: Brassica rapa

<400> SEQUENCE: 2

Met Lys Ser Ala Val Tyr Ala Leu Leu Cys Phe Ile Phe Ile Val Ser
1               5                   10                  15

Gly His Ile Gln Glu Leu Glu Ala Asn Leu Met Lys Arg Cys Thr Arg
            20                  25                  30

Gly Phe Arg Lys Leu Gly Lys Cys Thr Thr Leu Glu Glu Glu Lys Cys
        35                  40                  45

Lys Thr Leu Tyr Pro Arg Gly Gln Cys Thr Cys Ser Asp Ser Lys Met
    50                  55                  60

Asn Thr His Ser Cys Asp Cys Lys Ser Cys
65                  70

<210> SEQ ID NO 3
<211> LENGTH: 83
<212> TYPE: PRT
<213> ORGANISM: Brassica rapa
```

-continued

```
<400> SEQUENCE: 3

Met Lys Ser Ala Ile Tyr Ala Leu Leu Cys Phe Ile Phe Ile Val Ser
1               5                   10                  15

Ser His Val Gln Glu Val Ala Asn Leu Arg Lys Thr Cys Val His
            20                  25                  30

Arg Leu Asn Ser Gly Ser Cys Gly Lys Ser Gly Gln His Asp Cys
        35                  40                  45

Glu Ala Phe Tyr Thr Asn Lys Thr Asn Gln Lys Ala Phe Tyr Cys Asn
50                  55                  60

Cys Thr Ser Pro Phe Arg Thr Arg Tyr Cys Asp Cys Ala Ile Lys Cys
65                  70                  75                  80

Lys Val Arg

<210> SEQ ID NO 4
<211> LENGTH: 75
<212> TYPE: PRT
<213> ORGANISM: Brassica rapa

<400> SEQUENCE: 4

Met Lys Ser Ala Ile Tyr Ala Leu Leu Cys Phe Ile Phe Ile Ile Leu
1               5                   10                  15

Ser Arg Ser Gln Glu Leu Thr Glu Val Gly Ala Asp Lys Gln Gln Cys
            20                  25                  30

Lys Lys Asn Phe Pro Gly His Cys Glu Thr Ser Glu Arg Cys Glu Asn
        35                  40                  45

Thr Tyr Lys Arg Leu Asn Lys Lys Val Phe Asp Cys His Cys Gln Pro
50                  55                  60

Phe Gly Arg Arg Leu Cys Thr Cys Lys Cys
65                  70                  75

<210> SEQ ID NO 5
<211> LENGTH: 79
<212> TYPE: PRT
<213> ORGANISM: Brassica rapa

<400> SEQUENCE: 5

Met Lys Ser Val Leu Tyr Ala Leu Leu Cys Phe Ile Phe Ile Val Ser
1               5                   10                  15

Ser His Ala Gln Asp Val Glu Ala Asn Leu Met Asn Arg Cys Thr Arg
            20                  25                  30

Glu Leu Pro Phe Pro Gly Lys Cys Gly Ser Ser Glu Asp Gly Gly Cys
        35                  40                  45

Ile Lys Leu Tyr Ser Ser Glu Lys Lys Leu His Pro Ser Arg Cys Glu
50                  55                  60

Cys Glu Pro Arg Tyr Lys Ala Arg Phe Cys Arg Cys Lys Ile Cys
65                  70                  75

<210> SEQ ID NO 6
<211> LENGTH: 95
<212> TYPE: PRT
<213> ORGANISM: Brassica rapa

<400> SEQUENCE: 6

Met Arg Tyr Ala Thr Ser Ile Tyr Thr Phe Leu Thr Asn Ile His Tyr
1               5                   10                  15

Leu Cys Phe Ile Phe Leu Ile Leu Thr Tyr Val Gln Ala Leu Asp Val
            20                  25                  30
```

Gly Ala Trp Lys Cys Pro Glu Gly Ile Val Tyr Pro Ser Pro Ile Ser
            35                  40                  45

Gly Arg Cys Ile Asn Ser Arg Ser Thr Glu Cys Lys Lys His Tyr Glu
 50                  55                  60

Val Glu Gly Gln Asn Val Thr Asn Cys Arg Cys Asp Thr Tyr Ser Met
 65                  70                  75                  80

Gln Asn Pro Ala Arg Ile Thr Cys Tyr Cys Cys Lys Val Lys Ser
                85                  90                  95

```
<210> SEQ ID NO 7
<211> LENGTH: 30
<212> TYPE: DNA
<213> ORGANISM: artificial sequence
<220> FEATURE:
<223> OTHER INFORMATION: S8sp11-genome-Forward; Synthetic

<400> SEQUENCE: 7
ctgcaagtaa aagagagaat cttttatcac                                    30

<210> SEQ ID NO 8
<211> LENGTH: 21
<212> TYPE: DNA
<213> ORGANISM: artificial sequence
<220> FEATURE:
<223> OTHER INFORMATION: S8sp11-genome-Reverse; Synthetic

<400> SEQUENCE: 8
gcaccgcttc atcagatttg c                                             21

<210> SEQ ID NO 9
<211> LENGTH: 31
<212> TYPE: DNA
<213> ORGANISM: artificial sequence
<220> FEATURE:
<223> OTHER INFORMATION: SL-Forward 1; Synthetic

<400> SEQUENCE: 9
acacctcgga ctarawttta tgtattyttt c                                  31

<210> SEQ ID NO 10
<211> LENGTH: 32
<212> TYPE: DNA
<213> ORGANISM: artificial sequence
<220> FEATURE:
<223> OTHER INFORMATION: SL-Reverse 1; Synthetic

<400> SEQUENCE: 10
tcattaatat tttatatgca ctaatcgttt tg                                 32

<210> SEQ ID NO 11
<211> LENGTH: 27
<212> TYPE: DNA
<213> ORGANISM: artificial sequence
<220> FEATURE:
<223> OTHER INFORMATION: Class II-SP11-Forward; Synthetic

<400> SEQUENCE: 11
cgtgtgaaat aggcaattaa gtgcaag                                       27

<210> SEQ ID NO 12
<211> LENGTH: 26
<212> TYPE: DNA
<213> ORGANISM: artificial sequence
<220> FEATURE:
<223> OTHER INFORMATION: Class II-SP11-Reverse; Synthetic
```

-continued

<400> SEQUENCE: 12
ctttgcaaca gtagcaagta atcctc                                    26

<210> SEQ ID NO 13
<211> LENGTH: 25
<212> TYPE: DNA
<213> ORGANISM: artificial sequence
<220> FEATURE:
<223> OTHER INFORMATION: SL-Forward 2; Synthetic

<400> SEQUENCE: 13
taaccataga aaatattcg tgttc                                      25

<210> SEQ ID NO 14
<211> LENGTH: 21
<212> TYPE: DNA
<213> ORGANISM: artificial sequence
<220> FEATURE:
<223> OTHER INFORMATION: SLGI-Forward; Synthetic

<400> SEQUENCE: 14
agaacacttg tatctcccgg t                                         21

<210> SEQ ID NO 15
<211> LENGTH: 20
<212> TYPE: DNA
<213> ORGANISM: artificial sequence
<220> FEATURE:
<223> OTHER INFORMATION: SLGI-Reverse; Synthetic

<400> SEQUENCE: 15
catagtcgga tccgtgtttt                                           20

<210> SEQ ID NO 16
<211> LENGTH: 20
<212> TYPE: DNA
<213> ORGANISM: artificial sequence
<220> FEATURE:
<223> OTHER INFORMATION: SLGII-Forward; Synthetic

<400> SEQUENCE: 16
atgaaagggg tacagaacat                                           20

<210> SEQ ID NO 17
<211> LENGTH: 20
<212> TYPE: DNA
<213> ORGANISM: artificial sequence
<220> FEATURE:
<223> OTHER INFORMATION: SLGII-Reverse; Synthetic

<400> SEQUENCE: 17
ctcaagtccc actgctgcgg                                           20

<210> SEQ ID NO 18
<211> LENGTH: 24
<212> TYPE: DNA
<213> ORGANISM: artificial sequence
<220> FEATURE:
<223> OTHER INFORMATION: MLPK-Forward; Synthetic

<400> SEQUENCE: 18
gctacgaaaa tgtcttcgcc aatc                                      24

```
<210> SEQ ID NO 19
<211> LENGTH: 24
<212> TYPE: DNA
<213> ORGANISM: artificial sequence
<220> FEATURE:
<223> OTHER INFORMATION: MLPK-Reverse; Synthetic

<400> SEQUENCE: 19
cctagaattt gaaaggctgg atgc                                          24

<210> SEQ ID NO 20
<211> LENGTH: 31
<212> TYPE: DNA
<213> ORGANISM: artificial sequence
<220> FEATURE:
<223> OTHER INFORMATION: S60-sp11pro-Forward; Synthetic

<400> SEQUENCE: 20
ccgaagcttg acaacaaaga cggttctgat c                                  31

<210> SEQ ID NO 21
<211> LENGTH: 33
<212> TYPE: DNA
<213> ORGANISM: artificial sequence
<220> FEATURE:
<223> OTHER INFORMATION: S60-sp11pro-Reverse; Synthetic

<400> SEQUENCE: 21
cagccatggc ttatgagtat ataagatttt cgc                                33

<210> SEQ ID NO 22
<211> LENGTH: 26
<212> TYPE: DNA
<213> ORGANISM: artificial sequence
<220> FEATURE:
<223> OTHER INFORMATION: S52-Smi-Forward; Synthetic

<400> SEQUENCE: 22
ccatgcacca aataaatttc ctatgg                                        26

<210> SEQ ID NO 23
<211> LENGTH: 23
<212> TYPE: DNA
<213> ORGANISM: artificial sequence
<220> FEATURE:
<223> OTHER INFORMATION: S52-Smi-Reverse; Synthetic

<400> SEQUENCE: 23
gaatacacca agattgtgta gag                                           23
```

METHOD FOR BREEDING *BRASSICA RAPA* PLANT HAVING SELF-COMPATIBILITY

CROSS REFERENCE TO RELATED APPLICATIONS

This application is the U.S. National Phase of International Application No. PCT/JP2014/050958, filed Jan. 20, 2014, designating the U.S. and published in Japanese as WO 2014/0115680 A1 on Jul. 31, 2014, which claims the benefit of Japanese Patent Application No. 2013-011504, filed Jan. 24, 2013, the entire disclosures of which are hereby incorporated herein by reference.

REFERENCE TO SEQUENCE LISTING

This application incorporates by reference the sequence listing submitted as ASCII text filed via EFS-Web on Jul. 23, 2015. The Sequence Listing is provided as a file entitled "SEQLIST_LEX011.001APC.txt" which was created on Jul. 23, 2015 and last modified on Jul. 23, 2015, and which is 7,675 bytes in size.

TECHNICAL FIELD

The present invention relates to a technique that enables a self-incompatible Brassicaceae plant to be converted into self-compatible.

BACKGROUND ART

Brassicaceae plants include many plants whose entire plant bodies are edible, e.g., oilseed rape, turnip, Japanese mustard spinach, Chinese cabbage, bok choy, and Japanese radish, and for example, *Brassica rapa* includes a plant producing seeds having high utility value as a material for rapeseed oil. Conventionally, rapeseed oil has been used for food or lighting fuel, and in recent years, it receives attention as a material for biodiesel.

Currently, for production of rapeseed oil, *Brassica napus* is mainly used. *Brassica napus* is actively cultured in North America and Canada because it has self-compatibility and excellent seed productivity, however, growth and production efficiency thereof in other area is not good, and breed improvement is required. However, since *Brassica napus* is believed to be an amphidiploid species generated by natural crossbreeding between *Brassica rapa* and cabbages (*Brassica oleracea*), and has poor genetic diversity, it has been difficult to apply a conventional breeding method that introduces a beneficial gene by crossbreeding.

On the other hand, in Japan, *Brassica rapa* has been traditionally used as a material for rapeseed oil. *Brassica rapa* has immense genetic diversity, and has the potential of making advantageous strains in terms of the environmental suitability, improvement in seed productivity and so on. However, since *Brassica rapa* is self-incompatible and does not produce a seed in a single line, it is necessary to keep the lineage relying on natural crossbreeding by insects or the like in cooperative cultivation, and hence it is difficult to keep a specific lineage stably. Further, the seed productivity is low because crossbreeding with other individual is required to produce a seed, and breed improvement should be made on the whole mass to be crossbred, and hence it was difficult to breed an excellent lineage.

From such a background, there is a demand for a technique of converting self-incompatible Brassicaceae plants including *Brassica rapa* to ones having self-compatibility to thereby impart self seed fertility, and enabling efficient making and keeping of an excellent breed by utilizing the genetic diversity.

Here, self-incompatibility is one of the functions of suppressing self-pollination possessed by plants. This function causes self-other recognition between a pistil and pollen at the time of pollination, and allows pollination of only pollen of other individual. That is, in a plant having self-incompatibility, a seed is not formed when a pistil and pollen have the same genotype, because even if the pollen reaches the stigma, either of the stages including germination of pollen, growth of pollen tube, fertilization of ovule, and growth of fertilized embryo terminates. In many plants, such a function of self-incompatibility is controlled by a series of multiple allele cluster ($S_1$, $S_2$, ... $S_n$ haplotype) linked on a self-incompatibility gene locus (S gene locus). In a Brassicaceae plant, S haplotype encodes pollen factor SP11 which is to be a ligand, and a pistil factor SRK functioning as a receptor, and by specific interaction between SP11 and SRK on the same S gene, the own pollen is discriminated, and incompatible reaction occurs. Further, it is also known that stigma protein (SLG: S locus glycoprotein) exists on the S gene locus, which has a nucleotide sequence very similar to that of SRK protein, and is believed to function as a common receptor and extend the self-incompatibility.

Over 100 S haplotypes are known in Brassicaceae plants, and relation of dominance sometimes arises between two haplotypes. It has been revealed that in such a case, by the influence of an inverted transcription sequence (SMI) on the dominant S haplotype classified into class I, a SP11 expression regulation region on the recessive S haplotype classified into class II is DNA-methylated, and expression of the recessive S haplotype is completely suppressed (See, for example, Non-Patent Documents 1 and 2, and FIG. 1).

As described above, while various findings regarding the mechanism of self-incompatibility have been obtained, a practicable and convenient technique for efficiently converting a self-incompatible Brassicaceae plant to one having self-compatibility is still unknown.

PRIOR ART DOCUMENTS

Non-Patent Document

Non-Patent Document 1: Hiroshi Shiba et al., Develop. Growth Differ. (2012)54, 120-128
Non-Patent Document 2: Yoshiaki Tarutani et al., Nature, Vol. 466, 19 Aug. 2010, 983-986

SUMMARY OF THE INVENTION

Problems to be Solved by the Invention

It is a primary object of the present invention to provide a technique for converting a self-incompatible Brassicaceae plant to one having self-compatibility.

Means for Solving the Problem

The present inventors made diligent efforts to solve the aforementioned problem, and analyzed self-compatible variants of *Brassica rapa*, and found that $S_0$ haplotype ($S_0$ strain) in which pollen factor SP11 is deficient while an inverted repeat sequence (SMI) is retained in S haplotype belonging to class I on a self-incompatibility gene locus (S gene locus) in a Brassicaceae plant. The inventors also found that by crossbreeding a strain having $S_0$ haplotype and a self-incompatible Brassicaceae plant having S haplotype belonging to class II on a self-incompatibility gene locus, F1 progeny becomes a self-compatible strain that fails to express a pollen factor, and *Brassica rapa* having self seed fertility is obtained.

The present invention was accomplished as a result of further researches based on these findings. That is, the present invention provides a making method and a breeding method of a self-compatible Brassicaceae plant of the later-described form, a method for breeding a parent strain for F1 hybrid breeding of Brassicaceae plant, a method for screening a self-compatible Brassicaceae plant, a kit for screening, and so on.

Item 1. A method for making a self-compatible Brassicaceae plant from a self-incompatible Brassicaceae plant, comprising:

inactivating pollen factor SP11 while retaining an inverted repeat sequence (SMI) of $S_I$ haplotype belonging to class I in a self-incompatibility gene locus of Brassicaceae plant.

Item 2. The making method according to item 1, wherein the Brassicaceae plant is a *Brassica* plant.

Item 3. The making method according to item 2, wherein the *Brassica* plant is at least one *Brassica rapa* selected from the group consisting of oilseed rape, Chinese cabbage, turnip, Japanese mustard spinach, potherb mustard, bok choy, coleseed greens, and pak choi.

Item 4. A method for making a self-compatible Brassicaceae plant comprising the step (1a):

(1a) a step of crossbreeding a strain having $S_0$ haplotype belonging to class I in a self-incompatibility gene locus of Brassicaceae plant, in which pollen factor SP11 is inactivated while an inverted repeat sequence is retained, with a strain having $S_{II}$ haplotype belonging to class II to obtain a self-compatible strain.

Item 5. The breeding method according to item 4, further comprising the step (2a):

(2a) a step of selfing a Brassicaceae plant of the self-compatible strain obtained in the step (1a), or conducting inbreeding by using a strain having the same genotype with respect to S haplotype to select a strain that is a homozygote with respect to $S_0$ haplotype.

Item 6. The breeding method according to item 5, wherein the step (2a) is repeated five to seven times.

Item 7. A method for breeding a parent strain for F1 hybrid breeding of Brassicaceae plant comprising the steps (1b) to (3b):

(1b) a step of crossbreeding a strain having $S_0$ haplotype belonging to class I in a self-incompatibility gene locus of Brassicaceae plant, in which pollen factor SP11 is inactivated while an inverted repeat sequence is retained, and a strain having $S_{II}$ haplotype belonging to class II to obtain a self-compatible strain;

(2b) a step of selfing the self-compatible Brassicaceae plant obtained in the step (1b), or conducting inbreeding by using a strain having the same genotype with respect to S haplotype; and (3b) a step of selecting a strain that is a homozygote with respect to $S_{II}$ haplotype belonging to class II from strains obtained in the step (2b).

Item 8. The breeding method according to item 7, wherein the step (2b) is repeated five to seven times.

Item 9. A method of screening a self-compatible Brassicaceae plant, comprising the steps (1c) to (3c):

(1c) a step of preparing a DNA sample from a test Brassicaceae plant;

(2c) a step of amplifying DNA fragments containing nucleotide sequences encoding an inverted repeat sequence and SP11 from the DNA sample prepared in the step (1c); and (3c) a step of selecting a strain belonging to class I in a self-incompatibility gene locus of Brassicaceae plant, in which pollen factor SP11 is inactivated while an inverted repeat sequence is retained based on molecular weights or nucleotide sequences of the DNA fragments amplified in the step (2c).

Item 10. A kit for screening a self-compatible Brassicaceae plant, comprising:

(i) a regent capable of detecting retention of an inverted repeat sequence (SMI), and (ii) a reagent capable of detecting inactivation of pollen factor SP11 in $S_I$ haplotype belonging to class I on a self-incompatibility gene locus in Brassicaceae plant.

Item 11. Use of a strain of Brassicaceae plant having $S_0$ haplotype belonging to class I in a self-incompatibility gene locus, in which pollen factor SP11 is inactivated while an inverted repeat sequence is retained, and a strain of Brassicaceae plant having $S_{II}$ haplotype belonging to class II in a self-incompatibility gene locus for making a self-compatible Brassicaceae plant.

Effects of the Invention

According to the present invention, since expression of class II-SP11 gene is suppressed due to retention of the inverted repeat sequence (SMI) for SP11 gene of $S_{II}$ haplotype belonging to class II, and SP11 gene of $S_I$ haplotype belonging to class I is inactivated, it is possible to obtain a strain having self-compatibility because no pollen factor SP11 is expressed. In the present invention, since SP11 gene of class I is targeted for inactivation, the rate of obtaining a self-compatible strain increases as the crossbreeding with a strain having $S_{II}$ haplotype belonging to class II is repeated. Therefore, according to the method for making a self-compatible Brassicaceae plant of the present invention, it is possible to conduct conversion into a self-compatible strain efficiently and securely.

According to the method for breeding a self-compatible Brassicaceae plant of the present invention, it is possible to obtain a self-compatible Brassicaceae plant ($S_0S_{II}$ strain) by one crossbreeding because the F1 generation strain has self-compatibility. The self-compatible Brassicaceae plant obtained in this manner generally grows well due to heterosis, and has a large capsule, and shows high seed productivity. Therefore, by applying the technique of the present invention to a self-incompatible Brassicaceae plant with abundant gene resources, and selecting a self-compatible strain having high seed productivity therefrom, it is possible to provide a rapeseed for a material for food and biodiesel more efficiently with less labors than before.

In the course of selecting a strain showing high seed productivity, a pollinating operation such as bud pollination is not required because it has self-compatibility, and a strain showing high productivity can be selected from the strains that naturally produce a seed by itself. By repeating selection of a self-compatible strain that produces a seed by itself over five to seven generations, it is possible to fix traits such as seed productivity, and increase in proportion of self-compatible strain ($S_0S_0$ strain) that is a homozygote with respect to $S_0$ haplotype is expected, so that the obtained $S_0S_0$ strain subsequently retains the self-compatibility, and can be kept a single line by selfing.

Also according to breeding of a parent strain for F1 hybrid breeding of Brassicaceae plant of the present invention, it is possible to obtain an inbred line having recessive S haplotype homozygously without relying on bud pollination. Such an inbred line having a recessive S haplotype homozygously can be used as a parent strain for producing a F1 hybrid seed intended for heterosis.

The present invention also provides a method for screening a self-compatible Brassicaceae plant capable of screening a self-compatible strain efficiently, and a kit capable of carrying out the screening method conveniently.

EMBODIMENTS OF THE INVENTION (1) Method for Making Self Seed Fertile Brassicaceae Plant The method for making a self seed fertile Brassicaceae plant of the present invention is characterized by inactivating pollen factor SP11 while retaining an inverted repeat sequence (SMI) of dominant S haplotype belonging to class I in a self-incompatibility gene locus (S gene locus) of Brassicaceae plant, and as a result, it is possible to covert a self-incompatible Brassicaceae plant to one having self-compatibility, and to impart self seed fertility to the same.

In the present invention, a Brassicaceae plant refers to a plant classified into a dicotyledon, and having four petals arranged in the shape of a cross. In the present invention, as a Brassicaceae plant, for example, *Brassica* (rape) plants, *Raphanus* (Japanese radish) plants, Wasabia (wasabi) plants, Nasturtium (watercress) plants and so on can be recited, and *Brassica* plants are preferably exemplified.

Concrete examples of *Brassica* plants include *Brassica rapa* such as turnip rape (native rapeseed), Chinese cabbage, turnip, Japanese mustard spinach, potherb mustard, bok choy, coleseed greens, and pak choi; *Brassica oleracea* such as cabbage, broccoli, cauliflower, and brussels sprouts; and *Brassica juncea* such as brown mustard, and leaf mustard. Examples of *Raphanus* plants include Japanese radish, and radioxenon, examples of *Wasabia* plants include wasabi, and examples of *Nasturtium* plants include watercress.

Among these plants, *Brassica rapa* is more preferred because it has immense genetic diversity, and oilseed rape (native rapeseed) is further preferred.

In the present invention, a Brassicaceae plant includes the whole plant, pollen, seed; organs such as leaf, stem, root, floral organ, growing point, seed, and embryo; tissue such as epidermis, phloem, parenchyma, xylem, and vascular bundle; and plant culture cell or tissue such as protoplast and callus.

An inverted repeat sequence (SMI) refers to a sequence made up of 24 bases represented by the following SEQ ID NO: 1 located near the gene encoding pollen factor SP11 (for example, within about 100 kb upstream or downstream from the SP11 gene).

(SEQ ID NO: 1)
5'-ATGTTTACGTGTAAAATAGTTACA-3'

For example, regarding $S_9$ haplotype and $S_{12}$ haplotype, the position of the inverted repeat sequence on the gene has been identified, and regarding $S_9$ haplotype, it exists at 3.6 kb downstream from the untranslated region (utr) of SLG gene, and regarding $S_{12}$ haplotype, it exists at 3 kb downstream from the untranslated region (utr) of SLG gene. While the positions have not been identified for other S haplotypes, they can be determined based on existence of 24 bases represented by the above SEQ ID NO: 1.

Figure 1:
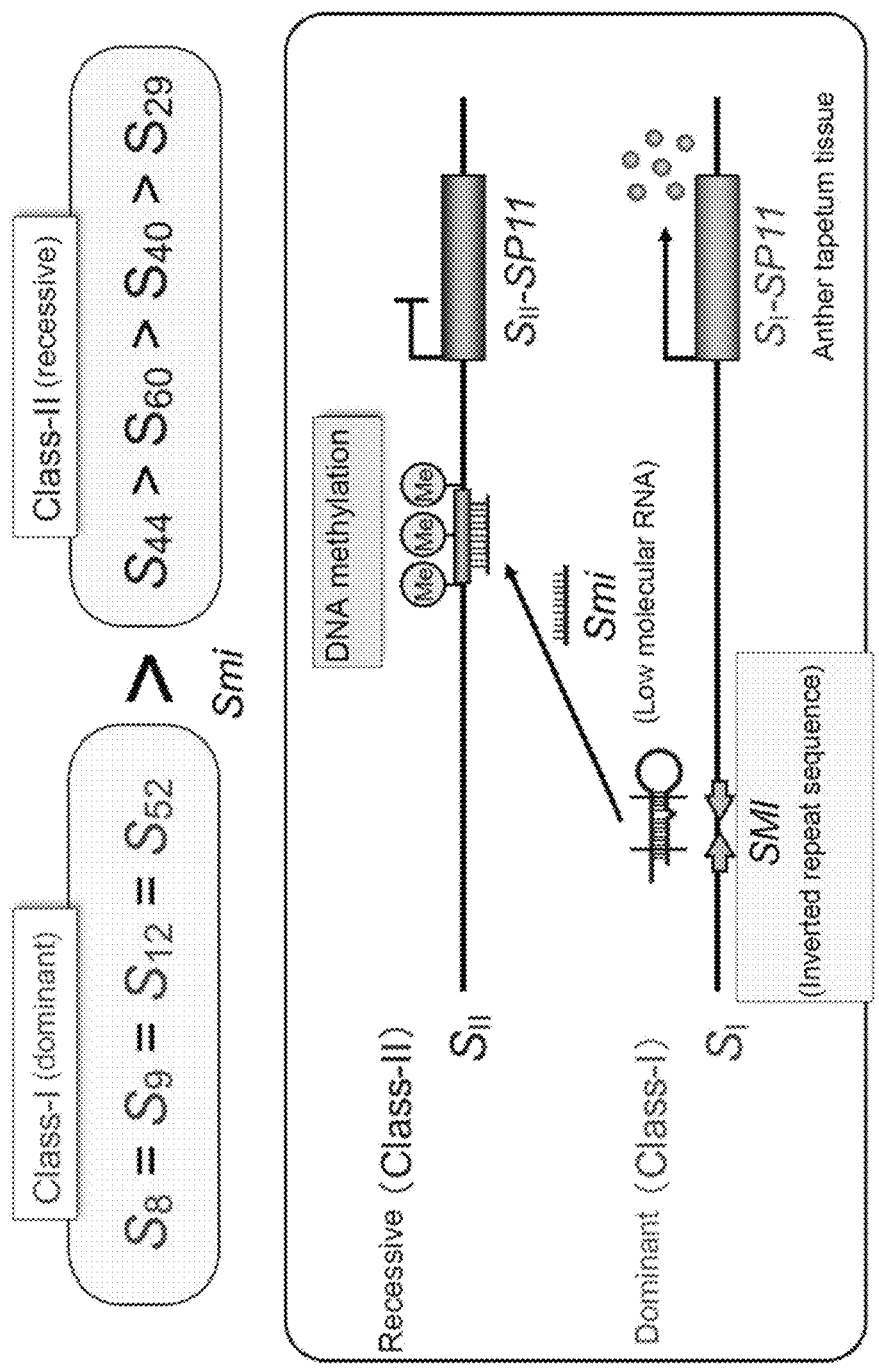
FIG. 1 is a diagram showing a dominance control mechanism between SP11 alleles.

It is believed that the relation of dominance between S haplotypes in Brassicaceae plants arises according to the following mechanism. That is, based on the inverted repeat sequence existing on class I $S_I$ haplotype, low molecular RNA made up of 24 nucleotides is produced, and a SP11 gene expression regulation region of $S_{II}$ haplotype belonging to class II having the homology is methylated, and thus expression of class II SP11 is suppressed to several tens of thousandths part. On the other hand, low molecular RNA homologous to a SP11 gene expression regulation region of class I $S_I$ haplotype is also synthesized from the inverted repeat sequence of class II $S_{II}$ haplotype, however, the SP11 gene expression regulation region is not methylated because homology with the target region is reduced due to single base substitution. With this mechanism, dominance arises in the reaction of self-other discrimination (see FIG. 1).

In the present description, $S_I$ haplotype belonging to class I is also indicated as dominant S haplotype. On the other hand, $S_{II}$ haplotype belonging to class II is also indicated as recessive S haplotype.

Pollen factor SP11 is expressed in an anther tapetum tissue, and is recognized by a pistil factor SRK which is a receptor, and self-incompatibility is established if they have the same genotype. The position on the S gene locus and the transcription direction of the gene encoding pollen factor SP11 differs between different S haplotypes, and many of these are not clearly identified, and, regarding $S_8$, $S_9$, $S_{12}$ haplotypes, for example, the position of SP11 gene on the S gene locus has been identified, and is located between pistil factors SRK and SLG in any cases (see Takayama et al., PNAS, vol. 97, no. 4, 2000, 1920-1925). Nucleotide sequences of individual S haplotypes of SP11 gene have already identified, and are registered in a known database. For example, they are registered in NCBI (National Center for Biotechnology Information, US) at accession number: AB035504.1 for $S_8$ haplotype, at accession number: AB022078.1 for $S_9$ haplotype, at accession number: AB035503.1 for $S_{12}$ haplotype, at accession number for $S_{52}$ haplotype: AB035505.1, and at accession number: AB067446.1 for $S_{60}$ haplotype. Therefore, based on these registered sequences, the position on the S gene locus of SP11 gene and so on can be identified.

While the form of inactivation of pollen factor SP11 is not particularly limited as far as it is the form in which SP11 is not recognized by SRK, it includes lack of expression of SP11 gene or lack of generation of normal SP11 protein while excluding reduction in expression of SP11 gene or protein in the present invention. Inactivation of pollen factor SP11 can be realized by modifying a gene encoding SP11 according to conventionally known genetic engineering techniques. Gene modification may be conducted on a gene itself, however, it may be conducted in any stages including transcription, post-transcriptional regulation, translation, and post-translational modification. An exemplary form of inactivation of SP11 includes the case where SP11 is not recognized by SRK as a result of introduction of mutation into the amino acid sequence constituting SP11 when a gene encoding SP11 is knocked out (or knocked in).

The means for knocking out (or knocking in) SP11 gene is not particularly limited as far as it does not allow transcription of mRNA from SP11 gene, and a conventionally known method can be employed, and for example, the following methods can be recited. That is, non-limiting exemplary methods include: after isolating SP11 gene (genomic DNA) from a plant for which gene modification is to be made (that is, self-incompatible Brassicaceae plant having at least a inverted repeat sequence (SMI) and SP11 gene) according to ordinary methods comprising, (a) inserting a DNA fragment containing a selective marker gene (for example, drug resistance gene or reporter gene) into a promotor region or an exon part of SP11 gene to destroy the function of the promotor or the exon; (b) cutting SP11 gene by using zinc finger nuclease (ZFNs) or Transcription Activator-Like Effector Nuclease (TALENs), etc. to introduce mutation into the gene; (c) inserting a stop codon into a region encoding SP11 protein to disable translation of complete protein; and (d) incorporating a DNA fragment that is constructed by inserting a transcription termination signal (for example, polyadenylation signal) into a transcription region to disable synthesis of complete mRNA, into a gene locus of a wild-type strain.

Also, it is possible to inactivate SP11 on the gene level by introducing function defective mutation such as point mutation, deficiency or frame shift mutation into SP11 gene by a mutagen treatment. While known means may be employed for the mutagen treatment, for example, irradiation including exposure to radiation (X-ray, γ-ray and so on), or heavy ion beam irradiation; and treatments with chemicals such as methyl methanesulfonate (EMS), ethylnitrosourea, nitrosoguanidine, benzopyrene and so on can be exemplified. In the present invention, it is preferred to employ a gene modification means for making deletion of SP11 gene.

As a method for introducing mutation into an amino acid sequence constituting SP11 to allow SP11 not to be recognized by SKR, a method of introducing mutation into amino acid residues that are highly conserved among S haplotypes is recited. In the amino acid residues constituting SP11 protein, eight cysteine residues, and two amino acid residues (concretely, a glycine residue at the second residue before the second cysteine residue from N-terminal, and an aromatic amino acid residue (phenylalanine residue or tyrosine residue) at the fourth residue after the third cysteine residue from N-terminal) are highly conserved (for example, see Mishima, M., et al., J. Biol. Chem. 278, 36389-36396, 2003 and so on). Therefore, it is supposed that by introducing mutation into a nucleotide sequence encoding that part, synthesis of complete SP11 protein is inhibited, and SP11 can be inactivated. The method for introducing mutation is not particularly limited as far as SP11 is inactivated, and conventionally known methods may be employed, and for example, site-directed mutagenesis can be recited.

For each S haplotype of SP11 protein, the amino acid sequence has been already identified, and registered in a known database. For example, amino acid sequences of $S_8$, $S_9$, $S_{12}$, $S_{52}$, $S_{60}$ haplotypes are concretely shown below.

```
S8-SP11 (GenBank; BAA92246.1: SEQ ID NO: 2);
MKSAVYALLCFIFIVSGHIQELEANLMKRCTRGFRKLGKCTTLEEEKCKT

LYPRGQCTCSDSKMNTHSCDCKSC

S9-SP11 (GenBank; BAA85458.1: SEQ ID NO: 3);
MKSAIYALLCFIFIVSSHVQEVEANLRKTCVHRLNSGGSCGKSGQHDCEA

FYTNKTNQKAFYCNCTSPFRTRYCDCAIKCKVR

S12-SP11 (GenBank; BAA92245.1: SEQ ID NO: 4);
MKSAIYALLCFIFIILSRSQELTEVGADKQQCKKNFPGHCETSERCENTY

KRLNKKVFDCHCQPFGRRRLCTCKC

S52-SP11 (GenBank; BAA92247.1: SEQ ID NO: 5);
MKSVLYALLCFIFIVSSHAQDVEANLMNRCTRELPFPGKCGSSEDGGCIK

LYSSEKKLHPSRCECEPRYKARFCRCKIC

S60-SP11 (GenBank; BAB86353.1: SEQ ID NO: 6);
MRYATSIYTFLTNIHYLCFIFLILTYVQALDVGAWKCPEGIVYPSPISGR

CINSRSTECKKHYEVEGQNVTNCRCDTYSMQNPARITCYCCKVKS
```

The "C" indicated in the amino acid sequence denotes eight cysteine residues conserved among S haplotypes, and the "G" and "Y" respectively denote a glycine residue and a tyrosine residue conserved among S haplotypes.

By transformation with an expression vector containing a DNA fragment encoding SP11 having mutation in the highly-conserved amino acid sequence, it is possible to obtain a Brassicaceae plant in which pollen factor SP11 is inactivated. In the expression vector, the DNA fragment encoding SP11 into which mutation is introduced may be linked with a promotor so as to allow expression.

For modifying SP11 gene by a genetic engineering technique, it is necessary to express it in an anther tapetum tissue. Therefore, a promotor capable of functioning in a cell of an objective plant is not particularly limited as far as it is a gene promotor expressed in an anther tapetum tissue of a plant body, and for example, SP11 promotor can be recited. The expression vector may have a known terminator region, a cis-regulatory element such as an enhancer, a drug resistance gene and so on as necessary. For facilitating mass preparation, the expression vector may contain a replication origin that enables self-replication in *Escherichia coli*, a selective marker (such as ampicillin resistance gene, or tetracycline resistance gene) in *Escherichia coli* and so on.

As a method for transforming a plant, conventionally known methods can be employed, and for example, by treating a plant to be transformed, with a cell wall degrading enzyme such as cellulase or hemicellulase to isolate a protoplast from the cell of the objective plant, and introducing an intended DNA fragment into the protoplast by PEG method, liposome method, electroporation or the like to cause redifferentiation into a plant body from the protoplast, it is possible to obtain a transformed plant body. Also on a cell of an objective plant having a cell wall, a direct introducing method such as micro injection method or particle gun method may be used. Further, transformation can be achieved by utilizing infection with *Agrobacterium*. In introducing an intended DNA fragment, the part of the plant body from which the cell is derived is not particularly limited, and an appropriate organ, tissue or cell can be selected depending on the employed method for introduction, and for example, an embryo, hypocotyl section, isolated growing point and so on can be recited. As a transformation method utilizing infection with *Agrobacterium*, for example, the method described in Takasaki et al., (1997) Breeding Science 47:127-13 can be employed.

The self-compatible Brassicaceae plant obtained by the making method of the present invention can be grown in conventionally known growing conditions, and the soil, fertilizer and so on to be used can be appropriately selected depending on the kind of the plant and the growth state.

As a condition for growing Brassicaceae plants, for example, a temperature ranging from 4 to 30° C., preferably ranging from 20 to 23° C.; a light quantity ranging from 400 to 100,000 Lux, preferably ranging from 1,000 to 50,000 Lux; an irradiation time ranging from 8 to 24 hours, preferably ranging from 12 to 14 hours; and a growing period ranging from 20 to 150 days, preferably ranging from 30 to 90 days can be recited.

Prior to sowing a seed of a Brassicaceae plant, the seed may be subjected to pretreatments such as disinfection and preliminary imbibition. The disinfecting treatment may be conducted according to a conventionally known method, and for example, it can be conducted by dipping in 5% sodium hypochlorite solution at 18 to 25° C. for 10 to 30 minutes. Also the preliminary imbibition treatment may be conducted according to a known method, and for example, a method of dipping in water at 18 to 25° C. for 1 to 24 hours can be recited. Preliminary imbibition may be conducted by spraying water to seeds, and water at 18 to 25° C. may be sprayed in an amount of 10 to 100 mL per 100 seeds, and left still for 1 to 24 hours. Also a low temperature treatment may be conducted as necessary. The condition of the low temperature treatment can be appropriately set from conventionally known conditions, and for example, the treatment can be carried out by growing seeds in an environment of 1 to 5° C. for 1 to 2 months.

As a method for confirming that pollen factor SP11 is inactivated while the inverted repeat sequence is retained in the self-compatible Brassicaceae plant made in the manner as described above, a method of preparing a DNA sample from the obtained plant individual according to an ordinary method, amplifying DNA fragments respectively encoding the inverted repeat sequence and SP11 by using primers and the DNA sample as a template, and judging from an amplified product according to the molecular weight and the nucleotide sequence can be recited.

Preparation of a DNA sample from a plant individual can be conducted by using a known method appropriately, and examples of such a method include a method based on phenol extraction and ethanol precipitation, and a method using glass beads. More conveniently, a commercially available DNA extraction reagent or DNA extraction kit may be used for preparation. Although the site of the plant body used in preparing a DNA sample is not particularly limited, for example, leaf is recited.

Also the method for obtaining DNA fragments encoding the inverted repeat sequence and SP11 from the prepared DNA sample can be a conventionally known method, and the DNA fragments encoding the inverted repeat sequence and SP11 can be specifically amplified by using primers.

A primer can be any oligonucleotide that has a characteristic sequence capable of specifically hybridizing with at least part of a target DNA fragment and amplifying the DNA fragment. Such a primer can be appropriately designed and synthesized based on sequence information of a target gene acquired by using a program such as BLAST or FASTA and a database. Nucleotide sequence length of a primer is generally 300 to 1500 bp, preferably 300 to 1000 bp, and more preferably 300 to 500 bp.

Examples of primer sequences to be used for confirming that SP11 gene is inactivated while the inverted transcription sequence (SMI) is retained in $S_I$ haplotype belonging to class I are shown below. Regarding SP11 gene, concrete nucleotide sequences are shown below while taking primers for SP11 gene of $S_8$ haplotype as examples.

Primer set for confirming existence of SP11 gene of $S_8$ haplotype

```
                                    (SEQ ID NO: 7)
S8sp11-genome-Forward;
5'-CTGCAAGTAAAAGAGAGAATCTTTTATCAC-3'

(SEQ ID NO: 8)
S8sp11-genome-Reverse;
5'-GCACCGCTTCATCAGATTTGC-3'
```

Primer set for confirming existence of SMI sequence of class I ($S_9$, $S_8$, $S_{12}$, $S_{52}$)
(see Tarutani, et al., (2010) Nature, vol. 466 (19), 983-986 Supplementary Table 5)

```
SL-Forward 1;
                                    (SEQ ID NO: 9)
5'-ACACCTCGGACTARAWTTTATGTATTYTTTC-3'

SL-Reverse 1;
                                    (SEQ ID NO: 10)
5'-TCATTAATATTTTATATGCACTAATCGTTTTG-3'
```

Concretely, SP11 gene of $S_{II}$ haplotype or the inverted repeat sequence belonging to class II can be confirmed respectively by the following primer sets.

Primer set for confirming existence of SP11 gene of class II ($S_{44}$, $S_{60}$, $S_{40}$, $S_{29}$)

```
                                    (SEQ ID NO: 11)
class II-SP11-Forward;
5'-CGTGTGAAATAGGCAATTAAGTGCAAG-3' class II-SP11-Reverse;
                                    (SEQ ID NO: 12)
5'-CTTTGCAACAGTAGCAAGTAATCCTC-3'
```

Primer set for confirming existence of SMI sequence ($S_{44}$, $S_{60}$, $S_{40}$, $S_{29}$) of class II
(see Tarutani, et al., (2010) Nature, vol. 466(19), 983-986 Supplementary Table 5)

```
SL-Forward 2;
                                    (SEQ ID NO: 13)
5'-TAACCATAGAAAAATATTCGTGTTC-3'

SL-Reverse 1;
                                    (SEQ ID NO: 10)
5'-TCATTAATATTTTATATGCACTAATCGTTTTG-3'
```

Based on the molecular weight or the nucleotide sequence of the amplified product obtained by amplification reaction of a DNA fragment using these primers, it is possible to confirm that the inverted repeat sequence is retained and SP11 is inactivated. For amplification of a DNA fragment, a conventionally known method can be employed, and non-limiting examples include polymerase chain reaction (PCR), and more concrete examples include RT-PCR, nested PCR, real-time PCR, and competitive PCR.

Inactivation of SP11 for $S_I$ haplotype belonging to class I can be confirmed, for example, by cutting the amplified DNA fragment with a restriction enzyme, and comparing the size of the cut DNA fragment with the molecular weight of the DNA fragment obtained from the plant body expressing normal SP11 by electrophoresis or the like. If the molecular weights of these fragments do not coincide with each other, it can be determined that SP11 is inactivated. Further, when SP11 gene is deleted, absence of the sequence can be confirmed by sequencing. By sequencing the DNA fragment, retention of the inverted repeat sequence can be confirmed.

Regarding SP11 gene of S haplotype belonging to class I, since the gene length (mainly length of intron) differs among S haplotypes ($S_9$, $S_8$, $S_{11}$, $S_{52}$ etc.), and the highly conserved part in the amino acid sequence is limited to the signal sequence of the first exon, it is difficult to design a common primer to confirm existence of almost every SP11 gene belonging to class I. Therefore, inactivation of SP11 gene of class I is desirably confirmed by designing primers based on the nucleotide sequence of SP11 gene of each S haplotype belonging to class I, and sequencing a DNA fragment amplified by these primers.

On the other hand, regarding SP gene of S haplotype and the inverted repeat sequence (SMI) belonging to class II, SP11 gene or the inverted repeat sequence can be amplified by a PCR method using common primer sets represented by the above SEQ ID NOs: 11 to 14, and existence can be confirmed based on the molecular weight and the nucleotide sequence.

The self-compatible Brassicaceae plant ($S_0$ strain) obtained by the making method of the present invention can be also acquired from a naturally occurring self-compatible variant of Brassicaceae plant. Concrete examples of such a variant include the one registered as *Brassica rapa* C634 in *Brassica* seed bank of TOHOKU UNIVERSITY. The $S_0$ strain originates from S54 haplotype of *Brassica rapa* C634.

Whether it is a heterozygote or a homozygote with respect to $S_0$ haplotype can be determined by using the primer sets represented by the following SEQ ID NOs: 15 to 18. That is, by using the primer sets represented by SEQ ID NOs: 14 and 15, almost every SLG (S-locus glycoprotein) belonging to class I including $S_0$ haplotype is amplified (SLG of class II is not amplified).

```
                                          (SEQ ID NO: 14)
SLGI-Forward: 5'-AGAACACTTGTATCTCCCGGT-3'

(SEQ ID NO: 15)
SLGI-Reverse: 5'-CATAGTCGGATCCGTGTTTT-3'
```

By using the primer sets represented by SEQ ID NOs: 16 and 17, SLG of class II is amplified (SLG of class I is not amplified).

```
                                           (SEQ ID NO: 16)
SLGII-Forward: 5'-ATGAAAGGGGTACAGAACAT-3'

(SEQ ID NO: 17)
SLGII-Reverse: 5'-CTCAAGTCCCACTGCTGCGG-3'
```

By means of the PCR method using these primer sets, it is possible to discriminate whether the obtained plant body is a homozygote or a heterozygote with respect to $S_0$ haplotype or $S_{II}$ haplotype. Further, the nucleotide sequence may be checked by sequencing as necessary.

The Brassicaceae plant obtained by the making method of the present invention is a self seed fertile plant which has been converted to one having self-compatibility. A strain ($S_0S_{II}$ strain) obtained by crossbreeding a strain having $S_0$ haplotype with a strain having $S_{II}$ haplotype belonging to class II retains self-compatibility, and grows well due to heterosis, and has high seed productivity. For example, a rapeseed having self-compatibility obtained by crossbreeding with a strain having $S_0$ haplotype by the method of the present invention usually has a larger size and number of capsule, a larger thickness and length of stem, a larger number of flowers, and a larger number of seeds per one capsule in comparison with the parent strain.

(2) Method for Breeding Brassicaceae Plant Having Self-Compatibility

The present invention provides a method for breeding a self-compatible Brassicaceae plant. The breeding method includes the following steps. (1a) a step of crossbreeding a strain having $S_0$ haplotype belonging to class I in which pollen factor SP11 is inactivated while the inverted repeat sequence is retained in a self-incompatibility gene locus of Brassicaceae plant, with a strain having S haplotype belonging to class II to obtain a self-compatible strain.

As the parent strains in step (1a), it is only required that a combination of a strain having $S_0$ haplotype and a strain having $S_{II}$ haplotype belonging to class II regarding S gene is selected, and each parent strain may be either a homozygote or a heterozygote with respect to S gene, and may be either self-compatible or self-incompatible.

The "crossbreeding" conducted in step (1a) means that regarding two strains of Brassicaceae plants having different origins, pollen of one strain pollinates to a stigma of the other strain, and then fertilization and seed formation advance. One exemplary method for crossbreeding includes covering the whole plants of two strains having different origins with a net bag, and releasing insects such as bees into the bag to allow pollination in the course that the insects collect nectar. Also artificial pollination may be conducted manually with brushes or tweezers. Further, a method of growing two masses of plural strains having different origins in a plastic greenhouse or the like, and releasing insects in the house to cause pollination (mass crossbreeding) may be employed.

In the crossbreeding conducted in step (1a), the strain having $S_0$ haplotype or the strain having $S_{II}$ haplotype used as a parent strain is not particularly limited regarding other genetic backgrounds than S gene, and may be appropriately arranged so that a strain having a desired phenotype and self-compatibility can be obtained by the crossbreeding. For example, by selecting a strain having a gene capable of expressing phenotypes such as increase in production amount of plant reserve substances such as oil, improvement in seed productivity, resistance to injurious insects, resistance to fungi, resistance to virus, resistance to bacteria, resistance to environmental stress (for example, resistance to cold), and improvement in nitrogen fixing ability, as a parent strain, it is possible to convert a Brassicaceae plant with such beneficial phenotypes to one having self-compatibility to impart it with self seed fertility.

As a more concrete example, it is possible to obtain a self-compatible $S_0S_{II}$ strain having resistance to cold and resistance to injurious insects by crossbreeding a strain having $S_0$ haplotype ($S_0$ strain) having resistance to cold, with a strain having $S_{II}$ haplotype ($S_{II}$ strain) having resistance to injurious insects. Alternatively, after obtaining a self-compatible $S_0S_{II}$ strain having resistance to cold by crossbreeding a $S_0$ strain and a $S_{II}$ strain having resistance to cold, the $S_0S_{II}$ strain as a parent strain may be crossbred with a $S_{II}$ strain having resistance to injurious insects to obtain a self-compatible $S_0S_{II}$ strain having resistance to cold and resistance to injurious insects.

The method for breeding a self-compatible Brassicaceae plant of the present invention may further include, after the step (1a), a step (2a) of selecting a strain that is a homozygote with respect to $S_0$ haplotype by selfing of the self-compatible strain of Brassicaceae plant obtained in the step (1a), or by conducting inbreeding using a strain having the same genotype with respect to S haplotype. Since the self-compatible Brassicaceae plant obtained in the step (1a) is a heterozygote with respect to $S_0$ haplotype, by selfing or inbreeding the strain, it is possible to obtain a strain that is a homozygote with respect to $S_0$ haplotype. When the present method is applied to *Brassica rapa*, the obtainable plant (*Brassica rapa*) can be preferably used for production of oil (rapeseed oil) because it has self seed fertility and seeds thereof can be harvested.

Here, "selfing" means that pollen of stamen pollinates to a stigma of pistil in the same flower, or pollen of a flower of a certain strain pollinates to a stigma of other flower of the same strain, and then fertilization and seed formation advance. One exemplary method for selfing includes covering one or plural inflorescences (mass of flowers) or the entirety of one strain with a net bag, and releasing insects such as bees in the bag to cause pollination. Also as described above, artificial pollination may be employed. Also a method of growing a plurality of strains of Brassicaceae plant originating from the same parent strain in a plastic greenhouse or the like, and releasing insects in the house to cause pollination between the plural strains (mass seed production) may be employed.

The term "inbreeding" used herein means conducting crossbreeding between brother strains made from the same parent strain. The crossbreeding can be conducted according to the method employed in the aforementioned selfing, and for example, a method of putting brother strains made from the same parent strain into a plastic greenhouse or the like, and conducting artificial pollination or pollination via insects can be recited.

In the method for breeding a self-compatible Brassicaceae plant of the present invention, selfing of the self-compatible strain of Brassicaceae plant conducted in the step (2a) may be repeated five to seven times, preferably six to seven times. In this technical field, it is believed that 99.9% of genes on genome become homozygotes by repeating selfing seven times. When selfing or inbreeding is repeated, a strain that is a homozygote with respect to $S_0$ haplotype can be selected from the strains obtained in the last selfing or inbreeding.

Therefore, by repeating the operation of selfing or inbreeding a strain of heterozygote ($S_0S_{II}$) obtained in the step (1a), selecting a self-compatible strain from the resultant strains, and further selfing or inbreeding the selected strain to select a self-compatible strain, almost every strain becomes a homozygote ($S_0S_0$) with respect to $S_0$ haplotype. Therefore, it is not necessarily required to confirm the genotype in discrimination of a homozygote, however, when discrimination is made on the basis of the genotype, it can be determined that the obtained self-compatible strain is a homozygote with respect to $S_0$ haplotype by confirming that the self-compatible strain (namely, having a genotype of either $S_0S_0$ or $S_0S_{II}$) does not have S haplotype of class II by a PCR method using the primer sets for confirming existence of class II-SP11 ($S_{44}$, $S_{60}$, $S_{40}$, $S_{29}$) described in the foregoing "(1) Method for making self seed fertile Brassicaceae plant".

(3) Method for Breeding Parent Strain for F1 Hybrid Breeding

The present invention also provides a method for breeding a parent strain for F1 hybrid breeding of Brassicaceae plant.

The breeding method includes the following steps.

(1b) a step of crossbreeding a strain having $S_0$ haplotype belonging to class I in which pollen factor SP11 is inactivated while the inverted repeat sequence is retained in a self-incompatibility gene locus of Brassicaceae plant, with a strain having $S_{II}$ haplotype belonging to class II to obtain a self-compatible strain;

(2b) a step of selfing the self-compatible strain of Brassicaceae plant obtained in the step (1b), or conducting inbreeding using a strain having the same genotype with respect to S haplotype; and (3b) a step of selecting a strain that is a homozygote with respect to $S_{II}$ haplotype belonging to class II from the strains obtained in the step (2b).

The step (1b) is equivalent to the step (1a) in the "(2) Method for breeding Brassicaceae plant having self-compatibility". In the step (2b), selfing of the self-compatible Brassicaceae plant obtained in the step (1b) is conducted, or inbreeding using a strain having the same genotype with respect to S haplotype is conducted, and selfing or inbreeding is as described in the foregoing "(2) Method for breeding Brassicaceae plant having self-compatibility".

In the step (2b), from the strains obtained by conducting selfing or inbreeding, a self-compatible strain having $S_0$ haplotype and $S_{II}$ haplotype heterozygously is selected. In the step (2b), selfing or inbreeding may be conducted repeatedly, and thus an inbred line that is genetically homogenous can be made. In the step (2b), by repeating selfing or inbreeding typically five to seven times, preferably six to seven times, a genetically homogenous strain is made.

Further, in the step (3b), from the strains obtained as a result of the last selfing or inbreeding in the step (2b), a self-incompatibility strain that is a homozygote with respect to $S_{II}$ haplotype is selected. The self-incompatibility strain obtained in this manner can be used as a parent strain for F1 hybrid breeding.

Selection of a strain that is a heterozygote or homozygote with respect to $S_{II}$ haplotype can be achieved by using primers designed based on known sequences of $S_{II}$ haplotype. As $S_{II}$ haplotype, for example, $S_{44}$, $S_{60}$, $S_{40}$, $S_{29}$ and so on can be recited, and sequences of these are disclosed, for example, in Kakizaki et al., (2006) Genes Genet. Syst. 81, 63-67. Discrimination between a heterozygote and a homozygote with respect to $S_{II}$ haplotype can be conducted, more concretely, by a PCR method using primer sets for confirming existence of class II-SP11 ($S_{44}$, $S_{60}$, $S_{40}$, $S_{29}$) as described in the foregoing "(1) Method for making self seed fertile Brassicaceae plant".

According to the method for breeding a parent strain for F1 hybrid breeding of the present invention, since a strain that is a homozygote with respect to recessive $S_{II}$ haplotype is obtained by selfing or inbreeding a self-compatible strain obtained in the step (1b), bud pollination that required enormous labor in the past is no longer needed, and a parent strain for F1 hybrid breeding can be bred conveniently and efficiently. Bud pollination means artificially pollinating to an immature pistil of an unflowered bud, and is a method utilizing the phenomenon that pollination to seed formation proceed without recognition of oneself due to immatureness of the stigma even in a self-incompatible plant.

(4) Method for Screening Self-Compatible Brassicaceae Plant

The present invention provides a method for screening a self-compatible Brassicaceae plant. The screening method is characterized by including the following steps (1c) to (3c).

(1c) a step of preparing a DNA sample from a test Brassicaceae plant;

(2c) a step of amplifying DNA fragments containing an inverted repeat sequence and SP11 sequence from the DNA sample prepared in the step (1c); and (3c) a step of selecting a strain belonging to class I in a self-incompatibility gene locus of Brassicaceae plant, in which pollen factor SP11 is inactivated while the inverted repeat sequence (SMI) is retained based on molecular weights or nucleotide sequences of the DNA fragments amplified in the step (2c).

Preparation of a DNA sample from a test Brassicaceae plant in the step (1c), a method for amplifying DNA fragments in the step (2c), and a method for selecting a strain in which pollen factor SP11 is inactivated while the inverted repeat sequence (SMI) is retained in the step (3c) are as described in the forgoing "(1) Method for making self-compatible Brassicaceae plant".

(5) Kit for Screening Self-Compatible Brassicaceae Plant

As described above, a strain of Brassicaceae plant belonging to class I in a self-incompatibility gene locus of Brassicaceae plant, in which pollen factor SP11 is inactivated while the inverted repeat sequence (SMI) is retained is found to have self-compatibility and self seed fertility. Based on this finding, the present invention further provides a kit for use in screening a self-compatible Brassicaceae plant. The kit includes (i) a regent capable of detecting retention of an inverted repeat sequence (SMI), and (ii) a reagent capable of detecting inactivation of pollen factor SP11 in $S_f$ haplotype belonging to class I on a self-incompatibility gene locus in Brassicaceae plant.

As such reagents, primers that specifically amplify DNA fragments encoding the inverted repeat sequence, and SP11 can be recited. Concrete examples of the reagents contained in the kit of the present invention include primers described in the foregoing "(1) Method for making self seed fertile Brassicaceae plant".

The screening kit of the present invention may further contain a buffer, salt, stabilizer, antiseptic and so on, and may be formulated according to a conventionally known method. The kit of the present invention may contain a reaction diluent, a cleaning agent, a reaction stopping liquid, a control sample and so on that are required to execute detection in addition to the aforementioned reagents.

Examples

Hereinafter, the present invention will be described by way of a test example, however, it is to be noted that the present invention is not limited to this.
1. Breeding of Self-Compatible Brassicaceae Plant
(1) Acquisition of Self-Compatibility Variant Strain ($S_0$ Strain)

A self-compatibility variant strain (*Brassica rapa* C634, available from TOHOKU UNIVERSITY, *Brassica* seed bank) is a self-compatible strain having variations both in a M gene locus and a S gene locus (see Murase et al., Science 303, 1516-1519, 2004; Fujimoto et al., Plant Mol. Biol. 61, 577-587, 2006). Here, M gene encodes a membrane-bound serine/threonine protein kinase named MLPK (M locus protein kinase). The membrane-bound serine/threonine protein kinase is believed to be an information transmission factor that positively transmits the information of self-incompatibility after reception of a signal of SP11 by SRK which is a receptor.

In a S gene locus in the present strain, base insertion in the first intron of S54-SRK (pistil factor) and base deletion in the S54-SP11 promotor region are confirmed. It was also demonstrated that the strain has S haplotype belonging to class I (S54 haplotype), and expression of SP11 is suppressed. Further, analysis of a registered genome sequence (GenBank: AB190354.1) revealed the retention of the SMI sequence of class I.

Figure 2:
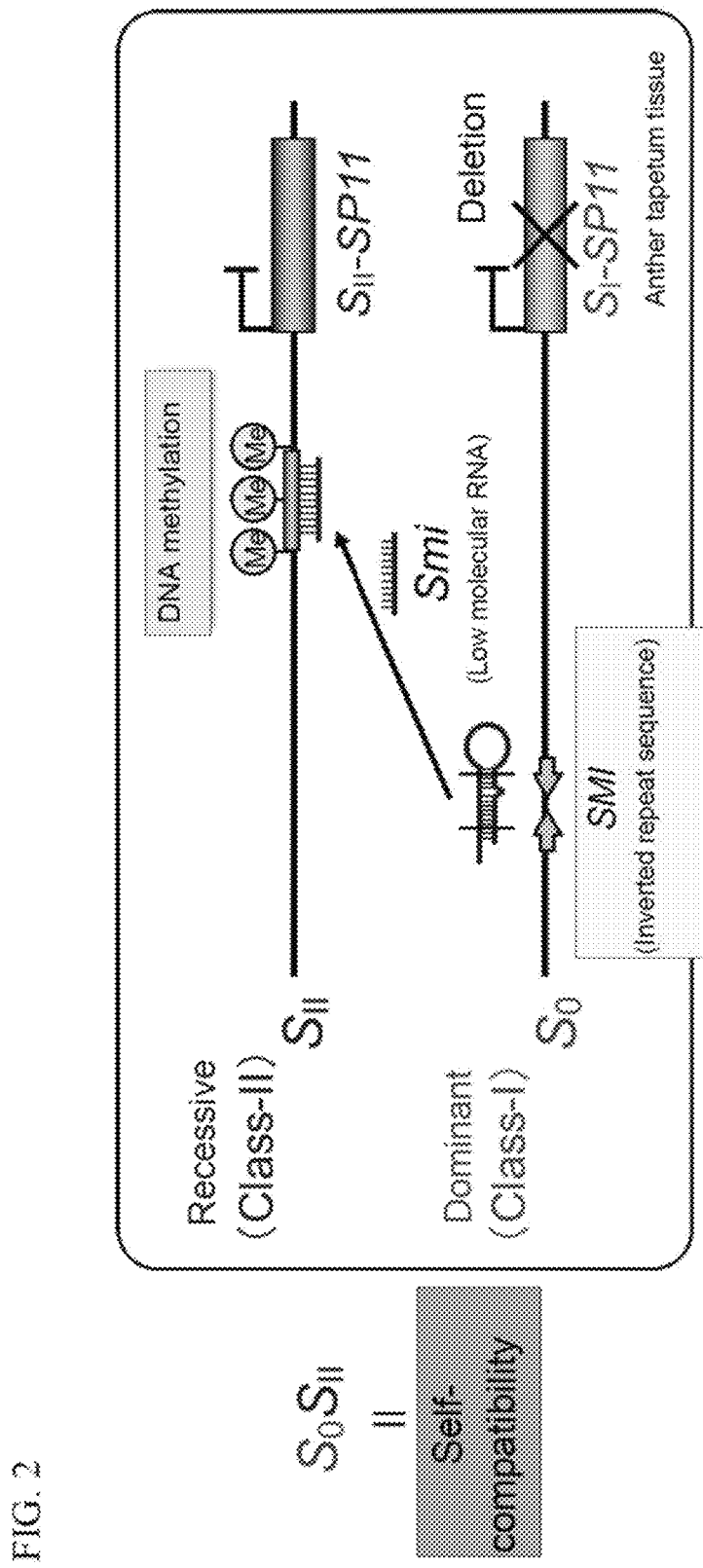
FIG. 2 is a diagram showing a self-compatibility expression mechanism by $S_0$ haplotype.

Then at first, the present strain $S_0S_0$mm and a self-incompatible wild-type strain $S_8S_8$MM are crossbred to make a F1 strain $S_0S_8$Mm, and the F1 strain was selfed by bud pollination to obtain F2 strains. While the F2 strains included self-compatible strains ($S_0S_0$MM, $S_0S_0$Mm, $S_0S_0$mm, $S_0S_0$mm, $S_8S_8$ mm), a strain not having variation in the M gene locus ($S_0S_0$MM) was selected by using a genomic PCR method, and the strain was selfed another five times to obtain a $S_0$ strain. It is conceivable that the $S_0$ strain is converted to one having self-compatibility by dominantly suppressing the function of recessive S haplotype belonging to class II (see FIG. 2).

For extraction of genomic DNA, DNeasy Plant Mini Kit (product of QIAGEN) was used, and extraction was conducted according to the attached protocol by using a lamina of a plant body as a sample. As primers for discriminating between M and m, the primer sets represented in the following SEQ ID NOs: 18 and 19 were used.

```
                                         (SEQ ID NO: 18)
MLPK-Forward: 5'-GCTACGAAAATGTCTTCGCCAATC-3'

(SEQ ID NO: 19)
MLPK-Reverse: 5'-CCTAGAATTTGAAAGGCTGGATGC-3'
```

The PCR reaction condition is as follows.

A cycle of dissociation at 95° C. for 20 seconds, annealing at 55° C. for 20 seconds, and elongation at 68° C. for 60 seconds was repeated 35 times. Under this PCR condition, about 300 bp is amplified in the case of M, and about 900 bp is amplified in the case of m.
(2) Acquisition of Self-Incompatible Brassicaceae Plant ($S_{60}S_{60}$ Strain)

As a $S_0S_{60}$ strain, a $S_{52}S_{60}$ strain of *Brassica rapa* cv. Osome (obtained from TAKII & CO., LTD.) was selfed by bud pollination, and a strain having $S_0S_{60}$ genotype was selected by using a genomic PCR method, and the strain was selfed another three times, and the strain thus obtained was used in the present example.

A primer set for amplifying $S_{60}$ is as follows. About 2 kbp is amplified by the PCR method using the primer set. The PCR condition is as described above.

```
$S_{60}$-sp11pro-Forward:
                                         (SEQ ID NO: 20)
5'-CCGAAGCTTGACAACAAAGACGGTTCTGATC-3'

$S_{60}$-sp11pro-Reverse:
                                         (SEQ ID NO: 21)
5'-CAGCCATGGCTTATGAGTATATAAGATTTTCGC-3'
```

A primer set for amplifying S52 is as follows. By the PCR method using the primer set, about 600 bp is amplified. The PCR condition is as described above.

```
                                         (SEQ ID NO: 22)
$S_{52}$-Smi-Forward: 5'-CCATGCACCAAATAAATTTCCTATGG-3'

(SEQ ID NO: 23)
$S_{52}$-Smi-Reverse: 5'-GAATACACCAAGATTGTGTAGAG-3'
```

(3) Culture Condition

A seed of *Brassica rapa* is allowed to germinate on a laboratory dish containing water-moisten gauze, and transplanted to a plug tray containing Metro Mix (Metro Mix 250: product of HYPONeX JAPAN CORP., LTD.) when the size reaches 2 to 3 cm. When seven to eight true leaves had emerged, the plant was transplanted to a black pot (9 cm diameter) containing organic compost (Organic compost for flowers and vegetables): product of Protoleaf corporation) and a low temperature treatment was conducted for a month in a low temperature room (temperature 4 to 5° C., luminous intensity: 200 to 300 Lux). Then the plant was transplanted into a No. 7 pot containing Hyuga soil (medium grain) (product of Hyuga-tsuchi Hanbai Co. Ltd.) spread over about one third of the capacity, and organic compost (Organic compost for flowers and vegetables: product of Protoleaf corporation), and cultured while herbicide spraying was appropriately conducted. As a $S_0$ strain or a $S_{60}$ strain, those after 2 to 5 months from sowing that had been cultured in an air-conditioned room (temperature 23 degrees, luminous intensity about 1000 Lux (light time), illumination time 12 hours/day) were used. Regarding the $S_0$ strain, it was cultured without conducting a low-temperature treatment because a breed whose genotype is fixed to rapid cycle (RC) causing early flowering was used for the $S_0$ strain.

(4) Crossbreeding Between $S_0$ Strain and $S_{60}$ Strain

Figure 3:
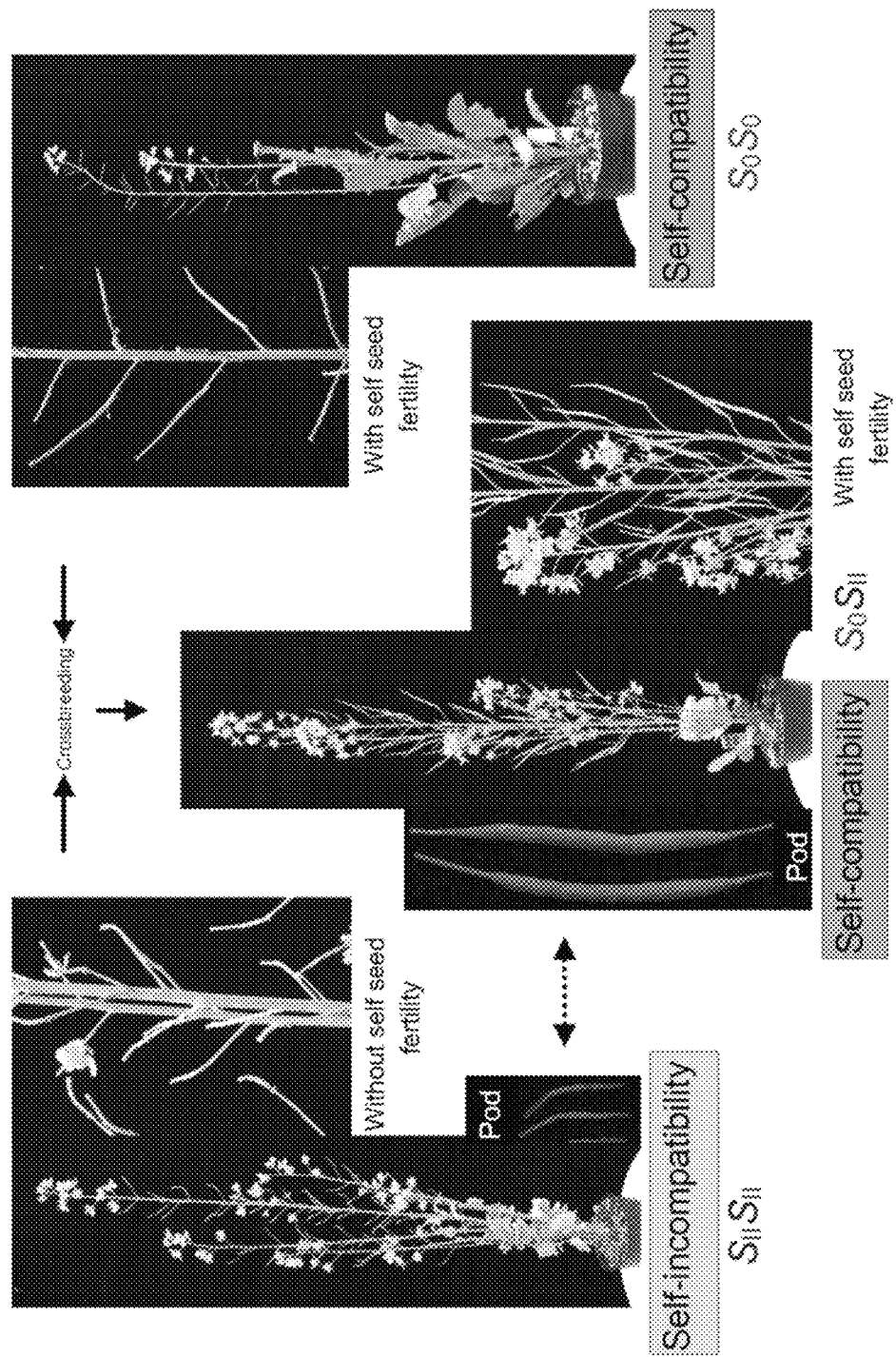
FIG. 3 is a representative picture showing an example of making a *Brassica rapa* having self seed fertility.

A *Brassica rapa* of $S_0$ strain ($S_0S_0$) and a *Brassica rapa* of self-incompatible ($S_{60}S_{60}$) strain were crossbred (once) by artificial pollination, and the obtained seed was cultured for 90 days under the same culture condition. Representative pictures of parent strains used in the crossbreeding and a self-compatible strain obtained as a result of the crossbreeding are shown in FIG. 3.

(5) Results

Figure 4:
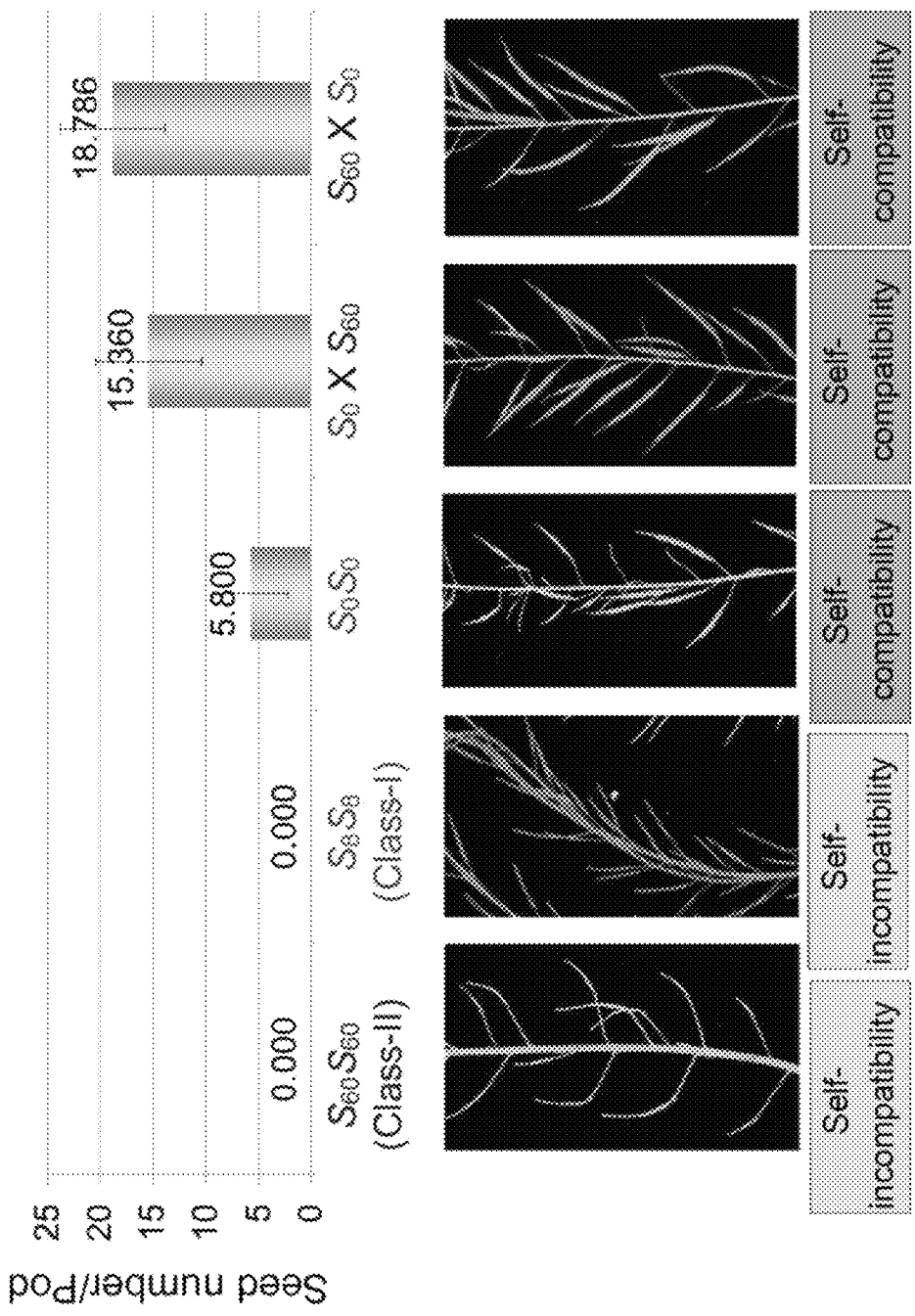
FIG. 4 is a graph showing the number of seeds sampled per one capsule in each *Brassica rapa* strain made in Examples, and representative pictures of individual strains.

The Brassicaceae plant ($S_0S_{60}$ strain) obtained in this manner lost self-incompatibility and had self seed fertility. Comparison of the number of seeds per one capsule revealed that the number of seeds per one capsule is larger in the strain having both $S_{60}$ and $S_0$ heterozygously than in the $S_0S_0$ strain (see FIG. 4). For comparison, the numbers of seeds per one capsule in the strain having S haplotype of class I homozygously ($S_8S_8$ strain) and the strain having S haplotype of class II homozygously ($S_{60}S_{60}$ strain) are also shown in the graph. Since these strains are self-incompatible, a seed is not formed.

Comparing $S_0S_{60}$ strain with the $S_{60}S_{60}$ strain or the $S_0S_0$ strain regarding the size and the number of capsule, the thickness and length of stem, and the number of flowers, the growth was apparently good in any terms. Such a phenotype is ascribable to the heterosis (see FIG. 3).

Sequence List Free Text

SEQ ID NO: 7 shows a nucleotide sequence of S8sp11-genome-Forward primer.

SEQ ID NO: 8 shows a nucleotide sequence of S8sp11-genome-Reverse primer.

SEQ ID NO: 9 shows a nucleotide sequence of SL-Forward 1 primer.

SEQ ID NO: 10 shows a nucleotide sequence of SL-Reverse 1 primer.

SEQ ID NO: 11 shows a nucleotide sequence of class II-SP11-Forward primer.

SEQ ID NO: 12 shows a nucleotide sequence of class II-SP11-Reverse primer.

SEQ ID NO: 13 shows a nucleotide sequence of SL-Forward 2 primer.

SEQ ID NO: 14 shows a nucleotide sequence of SLGI-Forward primer.

SEQ ID NO: 15 shows a nucleotide sequence of SLGI-Reverse primer.

SEQ ID NO: 16 shows a nucleotide sequence of SLGII-Forward primer.

SEQ ID NO: 17 shows a nucleotide sequence of SLGII-Reverse primer.

SEQ ID NO: 18 shows a nucleotide sequence of MLPK-Forward primer.

SEQ ID NO: 19 shows a nucleotide sequence of MLPK-Reverse primer.

SEQ ID NO: 20 shows a nucleotide sequence of $S_0$-sp11pro-Forward primer.

SEQ ID NO: 21 shows a nucleotide sequence of $S_0$-sp11pro-Reverse primer.

SEQ ID NO: 22 shows a nucleotide sequence of $S_{52}$-Smi-Forward primer.

SEQ ID NO: 23 shows a nucleotide sequence of $S_{52}$-Smi-Reverse primer.

What is claimed is:

1. A method for breeding a self-compatible *Brassica rapa* plant strain, comprising:

crossbreeding a *Brassica rapa* strain having an $S_0$ haplotype belonging to class I in a self-incompatibility gene locus of a self-incompatible *Brassica rapa* plant strain, in which a pollen factor SP11 is inactivated while an SP11 methylation inducer (SMI) inverted repeat sequence is retained, with a *Brassica rapa* strain having an $S_{II}$ haplotype belonging to class II, to obtain a self-compatible *Brassica rapa* plant strain, and selfing the self-compatible *Brassica rapa* plant strain, or conducting inbreeding of the self-compatible *Brassica rapa* plant strain by crossing it with a *Brassica rapa* plant strain having the same genotype as the self-compatible *Brassica rapa* plant strain with respect to an S haplotype, to select a *Brassica rapa* plant strain that is a homozygote with respect to the $S_0$ haplotype.

2. The method according to claim 1, wherein the selfing or inbreeding step is repeated about five to seven times.

3. A method for breeding a parent strain for an F1 hybrid breeding of a *Brassica rapa* plant strain, comprising:

(1b) crossbreeding a *Brassica rapa* plant strain having an $S_0$ haplotype belonging to class I in a self-incompatibility gene locus of a *Brassica rapa* plant strain, in which a pollen factor SP11 is inactivated while an SP11 methylation inducer (SMI) inverted repeat sequence is retained, with a *Brassica rapa* plant strain having an $S_{II}$ haplotype belonging to class II, to obtain a self-compatible *Brassica rapa* plant strain;

(2b) selfing the self-compatible *Brassica rapa* plant strain obtained in the step (1b), or conducting inbreeding by crossing it with a *Brassica rapa* plant strain having the same genotype as the self-compatible *Brassica rapa* plant strain with respect to an S haplotype, to obtain a set of *Brassica rapa* plant strains; and (3b) selecting a *Brassica rapa* plant strain that is a homozygote with respect to the $S_{II}$ haplotype belonging to class II from the set of *Brassica rapa* plant strains obtained in the step (2b).

4. The method according to claim 3, wherein the step (2b) is repeated about five to seven times.

* * * * *